United States Patent [19]

Sakata et al.

[11] Patent Number: 4,508,561
[45] Date of Patent: Apr. 2, 1985

[54] 1-PHENYLETHYL SULFONE DERIVATIVES OF 2-PYRIDYL-N-OXIDES AND HERBICIDAL COMPOSITIONS CONTAINING SAME

[75] Inventors: Gozyo Sakata; Tatsuo Numata; Kenzi Makino; Takuya Kakuta; Kazuya Kusano, all of Funabashi; Takasi Ikai; Tosihiko Oguti, both of Shiraoka, all of Japan

[73] Assignee: Nissan Chemical Industries Ltd., Tokyo, Japan

[21] Appl. No.: 457,381

[22] Filed: Jan. 12, 1983

[30] Foreign Application Priority Data

Jan. 22, 1982 [JP] Japan .................................. 57-8702

[51] Int. Cl.$^3$ .................. C07D 213/60; A01N 43/40
[52] U.S. Cl. ........................ 71/94; 546/294; 546/295
[58] Field of Search .............. 546/294, 295; 71/94

[56] References Cited

U.S. PATENT DOCUMENTS 3,960,542  6/1976  Plant et al. ........................ 71/94
4,438,271  3/1984  Bell et al. ........................ 546/294

OTHER PUBLICATIONS

March, Advanced Organic Chemistry: Reactions, Mechanisms and Structure McGraw-Hill, pub. pp. 20, 21, 357–359 (1968).

Primary Examiner—Alan L. Rotman
Attorney, Agent, or Firm—Oblon, Fisher, Spivak, McClelland & Maier

[57] ABSTRACT

1-Phenylethyl sulfone derivatives substituted by a halogenated alkyloxy group is represented by the general formula

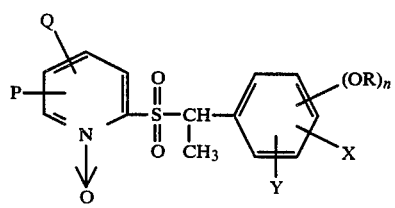

where R is an alkyl group substituted by a halogen atom, n is 1 or 2, each of P and Q is a hydrogen atom or a lower alkyl group and each of X and Y is a hydrogen atom, a lower alkyl group or a halogen atom. The compounds are effective as a herbicide. Also disclosed is a process for their preparation.

6 Claims, No Drawings

1-PHENYLETHYL SULFONE DERIVATIVES OF 2-PYRIDYL-N-OXIDES AND HERBICIDAL COMPOSITIONS CONTAINING SAME

BACKGROUND OF THE INVENTION

1. Field of the Invention

The present invention relates to novel 1-phenylethyl sulfone derivatives substituted by a halogenated alkyloxy group, a process for their preparation and herbicides containing them as an active ingredient.

More specifically, the present invention relates to (1) 1-phenylethyl sulfone derivatives substituted by a halogenated alkyloxy group, represented by the general formula (I)

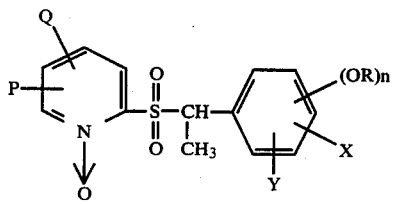

where R is an alkyl group substituted by a halogen atom, n is 1 or 2, each of P and Q is a hydrogen atom or a lower alkyl group and each of X and Y is a hydrogen atom, a lower alkyl group or a halogen atom;

(2) a process for preparing the 1-phenylethyl sulfone derivatives represented by the above formula (I) which comprises reacting a benzylsulfone derivative substituted by a halogenated alkyloxy group, represented by the general formula (II)

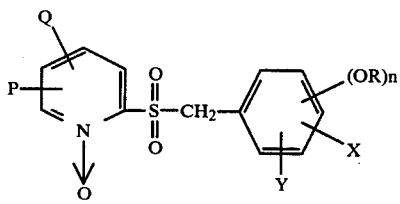

where R is an alkyl group substituted by a halogen atom, n is 1 or 2, each of P and Q is a hydrogen atom or a lower alkyl group and each of X and Y is a hydrogen atom, a lower alkyl group or a halogen atom, with a methylation agent, a polar aprotic solvent and a strong base; and (3) a herbicide containing at least one of the 1-phenylethyl sulfone derivatives represented by the formula (I) as an active ingredient.

The compounds of the present invention represented by the formula (I) are novel compounds having herbicidal activities and exhibit superior herbicidal effects against weeds such as grasses and Cyperus microiria when applied to the soil or foliage treatment. Further, they have a feature that they have little phytotoxicity against broad leaf crop plants such as cotton (*Gossypium indicum*), soybean (*Glycine max*), azuki bean (*Phaseolus angularis* Wight) kidney bean (*Phaseolus vulgaris* Linnaeus), sugar beet (*Beta vulgaris*), rape seed (*Brassica napus Linnaeus* var. *oleifera* De Candolle), peanut (*Arachis hypogaea* Linnaeus), sunflower (*Helianthus annuus*), Japanese radish (*Raphanus sativus* Linnaeus var. *acanthiformis* Makino), cabbage (*Brassica oleracea* Linnaeus var. *Capitata* Linnaeus), potato (*Solanum tuberosum* Linnaeus), eggplant (*Solanum melongena* Linnaeus). Accordingly, they are practically quite useful as an active ingredient of soil treating agents, soil miscible agents or foliage treating agents having selectivity, for broad leaf crop plants. Thus, the compounds of the present invention are most suitable for application to agricultural or horticultural fields, particularly as a herbicide for field application to selectively combat weeds such as grasses and Cyperus microiria for the cultivation of broad leaf crop plants. In addition to the application to the agricultural or horticultural fields such as a up-land field, a paddy field or an orchard, the compounds of the present invention can be applied to combat various weed in noncultivated lands such as a playground, vacant land or railroad sides. Their dosage may vary depending upon the particular site for application, the season for application, the manner of the application, the types of the weeds to be combated or the type of cultivated plant. However, they are usually applied in an effective amount of from 0.05 to 10 kg per hectare.

2. Description of the Prior Art

It is known that a benzylsulfonylpyridine-N-oxide represented by the general formula (III)

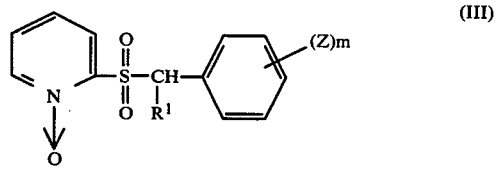

where $R^1$ is a hydrogen atom or a $C_1$–$C_{15}$ alkyl group, Z is a hydrogen atom, a halogen atom, a $C_1$–$C_3$ alkyl group, a nitro group, a cyano group, a $C_1$–$C_2$ alkyloxy group, a —$CF_3$ group, a 2,2-dichlorocyclopropyl group, a phenyl group, a methylenedioxy group, a vinyl group or a phenyloxy group and m is an integer of from 1 to 5, has herbicidal activities, for instance, from U.S. Pat. Nos. 3,960,542, 4,019,893 and 4,050,921.

Further, it is known from published European patent application No. 36-638 that a benzylsulfonylpyridine-N-oxide represented by the general formula (IV)

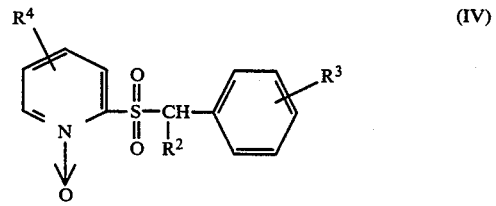

where $R^2$ is a hydrogen atom or a methyl group, $R^3$ is a hydrogen atom, a halogen atom, a $C_1$–$C_4$ alkyl group, a cyano group, a —$CF_3$ group or a nitro group and $R^4$ is a hydrogen atom, a $C_1$–$C_4$ alkyl group, a phenyl group or a cyano group, has herbicidal activities.

The the compounds of the present invention represented by the general formula (I) i.e. 1-phenylethylsulfonylpyridine-N-oxide derivatives where a halogenated alkyloxy group is introduced in the benzene ring of the benzylsulfonylpyridine-N-oxide, are not included in the prior art represented by the above general formulas (III) and (IV), and they are novel compounds. Further, it has been found that by the introduction of the halogenated alkyloxy group into the benzene ring of the benzylsulfonylpyridine-N-oxide, the herbicidal activities can substantially be increased and the phytotoxicity against the crop plants can be minimized as compared with the conventional benzylsulfonylpyridine-N-oxide derivatives represented by the general formula (III) and containing an alkyloxy group such as a methoxy group or an alkyl group substituted by a halogen atom such as a —CF$_3$ group instead of the halogenated alkyloxy group.

DESCRIPTION OF THE PREFERRED EMBODIMENTS

The present invention has been accomplished on the basis of the above discovery and provides (1) 1-phenylethyl sulfone derivatives substituted by a halogenated alkyloxy group represented by the general formula (I), (2) a process for their preparation and (3) a herbicide containing the 1-phenylethyl sulfone derivatives of the general formula (I) as an active ingredient.

The 1-phenylethyl sulfone derivatives of the formula (I) of the present invention can readily be prepared by reacting a benzyl sulfone derivative substituted by a halogenated alkyloxy group, represented by the general formula (II) with a methylation agent, a polar aprotic solvent and a strong base to methylate the methylene group, as shown by the following reaction formula:

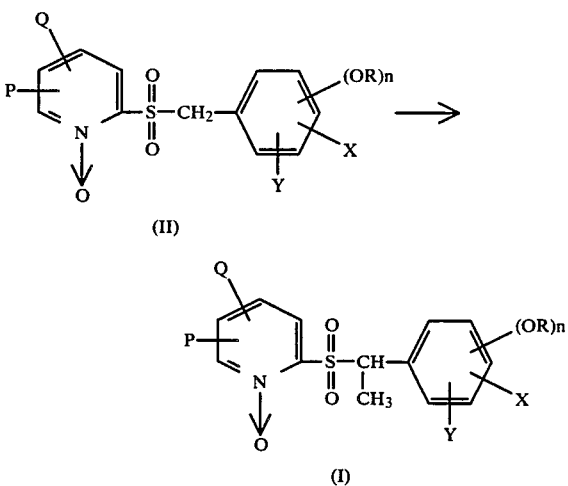

where R, P, Q, X, Y and n are as defined above.

As the methylation agent, there may be used, for instance, methyl chloride, methyl bromide, methyl iodide or dimethyl sulfate. As the polar aprotic solvent, there may preferably be used N,N-dimethylformamide, tetrahydrofuran or diethylether. As the strong base, there may be used, for instance, sodium hydride, sodium amide or sodium hydroxide. The reaction temperature is not critical, and the reaction may be conducted at a temperature from 0° C. to 40° C. The reaction time may vary depending upon the reactants and the reaction temperature, but it is usually from 20 minutes to 4 hours. After the reaction, the desired product can be isolated in a usual manner whereby a 1-phenylethyl sulfone derivative substituted by a halogenated alkyloxy group, represented by the formula (I) can be obtained in good yield and with high purity. If required, the product can further be purified by a column chromatography or recrystallization. The compound represented by the general formula (II) as the starting material can readily be prepared in accordance with the following reaction formulas:

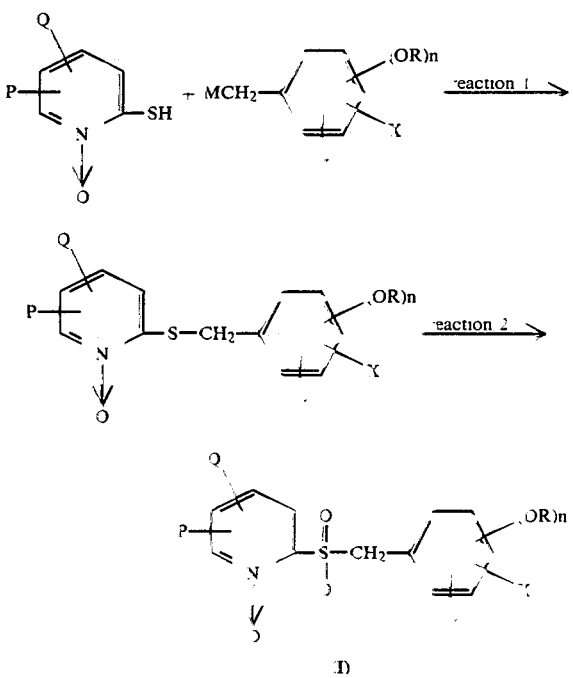

where R, P, Q, X, Y and n are as defined above and m is a chlorine atom or a bromine atom. The 2-mercaptopyridine-N-oxide used in the reaction 1 can be prepared in accordance with the process described in U.S. Pat. No. 3,159,640. The benzyl halide having a halogenated alkyloxy group as a substituent can be prepared in accordance with the process described in Japanese Unexamined Patent Publication No. 33495/1980. Reaction 1 proceeds quantitatively if the 2-mercaptopyridine-N-oxide is reacted with a stoichiometric amount of benzyl halide in the presence of a base. Then, in reaction 2, a stoichiometric amount or an excess amount of a peroxide such as hydrogen peroxide, peracetic acid or m-chloroperbenzoic acid is used for oxidation, whereby a benzyl sulfone derivative substituted by a halogenated alkyloxy group represented by the general formula (II) can be quantitatively prepared.

Further, the compound of the formula (I) of the present invention can readily be prepared by the reaction as shown below:

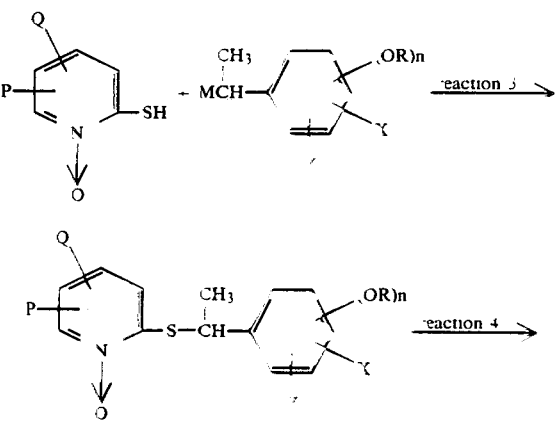

-continued

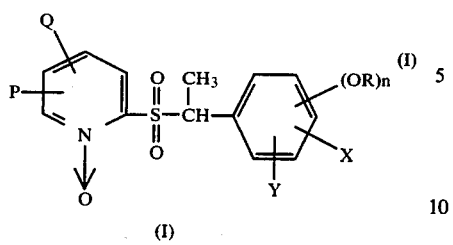

where R, P, Q, X, Y, M and n are as defined above.

Reaction 3 can be carried out with good yield (yield of 47–91%) by reacting the 2-mercaptopyridine-N-oxide derivative with a stoichiometric amount of 1-phenylethyl halide derivative. Then, in reaction 4, a stoichiometric amount or an excess amount of a peroxide such as hydrogen peroxide, a mixture of hydrogen peroxide and a metal salt, peracetic acid, perbenzoic acid or m-chloroperbenzoic acid is used for the oxidation, whereby a 1-phenylethyl sulfone derivative substituted by a halogenated alkyloxy group represented by the formula (I) can be prepared in good yield.

Typical examples of the compounds of the present invention are given in Table 1. However, it should be understood that these examples are given for the purpose of illustration only and they by no means restrict the scope of the compounds of the present invention.

TABLE 1

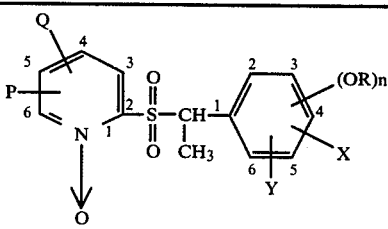

| Comp. No. | RO | n | X | Y | P | Q |
|---|---|---|---|---|---|---|
| 1 | 2-CHF$_2$O | 1 | H | H | H | H |
| 2 | 3-CHF$_2$O | 1 | H | H | H | H |
| 3 | 4-CHF$_2$O | 1 | H | H | H | H |
| 4 | 2-CF$_3$CH$_2$O | 1 | H | H | H | H |
| 5 | 3-CF$_3$CH$_2$O | 1 | H | H | H | H |
| 6 | 2-FCH$_2$CH$_2$O | 1 | H | H | H | H |
| 7 | 3-FCH$_2$CH$_2$O | 1 | H | H | H | H |
| 8 | 2-F(CH$_2$)$_3$O | 1 | H | H | H | H |
| 9 | 2-CHF$_2$CF$_2$O | 1 | H | H | H | H |
| 10 | 3-CHF$_2$CF$_2$O | 1 | H | H | H | H |
| 11 | 2-CHClFCF$_2$O | 1 | H | H | H | H |
| 12 | 2-CHCl$_2$CF$_2$O | 1 | H | H | H | H |
| 13 | 2-CHF$_2$O | 1 | 3-Cl | H | H | H |
| 14 | 2-CHF$_2$O 5-CHF$_2$O | 2 | H | H | H | H |
| 15 | 2-CHF$_2$O | 1 | 5-Cl | H | H | H |
| 16 | 2-CHF$_2$O 6-CHF$_2$O | 2 | H | H | H | H |
| 17 | 2-CHF$_2$O | 1 | 5-F | H | H | H |
| 18 | 2-CHF$_2$O | 1 | 5-Br | H | H | H |
| 19 | 2-CHF$_2$O | 1 | 5-CH$_3$ | H | H | H |
| 20 | 2-CHF$_2$O | 1 | 5-C$_2$H$_5$ | H | H | H |
| 21 | 2-CHF$_2$O | 1 | 5-tBu | H | H | H |
| 22 | 2-CHF$_2$O | 1 | 3-tBu | H | H | H |
| 23 | 3-CHF$_2$O | 1 | 6-Cl | H | H | H |
| 24 | 3-CHF$_2$O 4-CHF$_2$O | 2 | H | H | H | H |
| 25 | 3-CHF$_2$O | 1 | 6-F | H | H | H |
| 26 | 3-CHF$_2$O | 1 | 6-CH$_3$ | H | H | H |
| 27 | 2-CF$_3$CH$_2$O | 1 | 5-Cl | H | H | H |
| 28 | 2-CF$_3$CH$_2$O 5-CF$_3$CH$_2$O | 2 | H | H | H | H |
| 29 | 2-CF$_3$CH$_2$O 6-CF$_3$CH$_2$O | 2 | H | H | H | H |
| 30 | 3-CF$_3$CH$_2$O | 1 | 6-Cl | H | H | H |
| 31 | 2-CF$_3$CH$_2$O | 1 | 5-F | H | H | H |
| 32 | 2-CF$_3$CH$_2$O | 1 | 5-Br | H | H | H |
| 33 | 2-CF$_3$CH$_2$O | 1 | 5-CH$_3$ | H | H | H |
| 34 | 2-CF$_3$CH$_2$O | 1 | 5-C$_2$H$_5$ | H | H | H |
| 35 | 2-CF$_3$CH$_2$O | 1 | 5-tBu | H | H | H |
| 36 | 3-CF$_3$CH$_2$O | 1 | 6-F | H | H | H |
| 37 | 3-CF$_3$CH$_2$O | 1 | 6-CH$_3$ | H | H | H |
| 38 | 2-ClCH$_2$CH$_2$O | 1 | 5-Cl | H | H | H |
| 39 | 3-ClCH$_2$CH$_2$O | 1 | 6-Cl | H | H | H |
| 40 | 2-Cl(CH$_2$)$_3$O | 1 | 5-Cl | H | H | H |
| 41 | 2-CHF$_2$CF$_2$O | 1 | 5-Cl | H | H | H |
| 42 | 2-CHClFCF$_2$O | 1 | 5-Cl | H | H | H |
| 43 | 2-CHCl$_2$CF$_2$O | 1 | 5-Cl | H | H | H |
| 44 | 2-CHF$_2$O | 1 | 3-Cl | 5-Cl | H | H |
| 45 | 2-CHF$_2$O | 1 | 3-Cl | 5-Br | H | H |
| 46 | 2-CHF$_2$O | 1 | H | H | 3-CH$_3$ | H |
| 47 | 2-CHF$_2$O | 1 | 5-Cl | H | 3-CH$_3$ | H |
| 48 | 3-CHF$_2$O | 1 | 6-Cl | H | 3-CH$_3$ | H |
| 49 | 2-CF$_3$CH$_2$O | 1 | 5-Cl | H | 3-CH$_3$ | H |
| 50 | 2-CHF$_2$CF$_2$O | 1 | 5-Cl | H | 3-CH$_3$ | H |
| 51 | 2-CHF$_2$O | 1 | H | H | 4-CH$_3$ | H |
| 52 | 2-CHF$_2$O | 1 | 5-Cl | H | 4-CH$_3$ | H |
| 53 | 2-CHF$_2$O 5-CHF$_2$O | 2 | H | H | 4-CH$_3$ | H |
| 54 | 2-CHF$_2$O 6-CHF$_2$O | 2 | H | H | 4-CH$_3$ | H |
| 55 | 2-CHF$_2$O | 1 | 5-F | H | 4-CH$_3$ | H |
| 56 | 2-CHF$_2$O | 1 | 5-Br | H | 4-CH$_3$ | H |
| 57 | 2-CHF$_2$O | 1 | 5-CH$_3$ | H | 4-CH$_3$ | H |
| 58 | 3-CHF$_2$O | 1 | 6-Cl | H | 4-CH$_3$ | H |
| 59 | 2-CF$_3$CH$_2$O | 1 | 5-Cl | H | 4-CH$_3$ | H |
| 60 | 2-CF$_3$CH$_2$O 6-CF$_3$CH$_2$O | 2 | H | H | 4-CH$_3$ | H |
| 61 | 2-CF$_3$CH$_2$O | 1 | 5-F | H | 4-CH$_3$ | H |
| 62 | 2-CF$_3$CH$_2$O | 1 | 5-Br | H | 4-CH$_3$ | H |
| 63 | 2-CF$_3$CH$_2$O | 1 | 5-CH$_3$ | H | 4-CH$_3$ | H |
| 64 | 3-CF$_3$CH$_2$O | 1 | 6-Cl | H | 4-CH$_3$ | H |
| 65 | 2-FCH$_2$CH$_2$O | 1 | 5-Cl | H | 4-CH$_3$ | H |
| 66 | 2-CHF$_2$CF$_2$O | 1 | 5-Cl | H | 4-CH$_3$ | H |
| 67 | 2-CHF$_2$O | 1 | 5-Cl | H | 4-tBu | H |
| 68 | 2-CF$_3$CH$_2$O | 1 | 5-Cl | H | 4-tBu | H |
| 69 | 2-CHF$_2$CF$_2$O | 1 | 5-Cl | H | 4-tBu | H |
| 70 | 2-CHF$_2$O | 1 | 5-Cl | H | 3-CH$_3$ | 4-CH$_3$ |
| 71 | 2-CHF$_2$O | 1 | 5-F | H | 3-CH$_3$ | 4-CH$_3$ |
| 72 | 2-CHF$_2$O | 1 | 5-CH$_3$ | H | 3-CH$_3$ | 4-CH$_3$ |
| 73 | 2-CF$_3$CH$_2$O | 1 | 5-F | H | 3-CH$_3$ | 4-CH$_3$ |
| 74 | 2-CF$_3$CH$_2$O | 1 | 5-CH$_3$ | H | 3-CH$_3$ | 4-CH$_3$ |
| 75 | 2-CF$_3$CH$_2$O | 1 | 5-Cl | H | 3-CH$_3$ | 4-CH$_3$ |
| 76 | 2-CHF$_2$O | 1 | 5-Cl | H | 4-CH$_3$ | 5-CH$_3$ |
| 77 | 2-CHF$_2$O | 1 | 5-F | H | 4-CH$_3$ | 5-CH$_3$ |
| 78 | 2-CHF$_2$O | 1 | 5-CH$_3$ | H | 4-CH$_3$ | 5-CH$_3$ |
| 79 | 2-CF$_3$CH$_2$O | 1 | 5-Cl | H | 4-CH$_3$ | 5-CH$_3$ |
| 80 | 2-CF$_3$CH$_2$O | 1 | 5-F | H | 4-CH$_3$ | 5-CH$_3$ |
| 81 | 2-CF$_3$CH$_2$O | 1 | 5-CH$_3$ | H | 4-CH$_3$ | 5-CH$_3$ |
| 82 | 2-CHF$_2$O | 1 | 5-Cl | H | 5-CH$_3$ | H |
| 83 | 2-CF$_3$CH$_2$O | 1 | 5-Cl | H | 5-CH$_3$ | H |
| 84 | 2-CHF$_2$O | 1 | 6-Cl | H | 5-CH$_3$ | H |
| 85 | 2-CHF$_2$O | 1 | 5-Cl | H | 6-CH$_3$ | H |
| 86 | 2-CHF$_2$O | 1 | 5-Cl | H | 3-C$_2$H$_5$ | 6-CH$_3$ |
| 87 | 2-CF$_3$CH$_2$O | 1 | 5-Cl | H | 3-C$_2$H$_5$ | 6-CH$_3$ |
| 88 | 2-CF$_3$CH$_2$O | 1 | 5-C$_2$H$_5$ | H | 4-CH$_3$ | H |

When the compounds of the present invention are to be used as herbicides, they are usually mixed with a suitable carrier, for instance, a solid carrier such as clay, talc, bentonite or diatomaceous earth, or a liquid carrier such as water, an alcohol (such as methanol or ethanol), an aromatic hydrocarbon (such as benzene, toluene or xylene), a chlorinated hydrocarbon, an ether, a ketone, an ester (such as ethyl acetate) or an acid amide (such as dimethylformamide). If desired, an emulsifier, a dispersing agent, a suspending agent, a penetrating agent, a spreader or a stabilizer may be added to prepare an optional formulation such as a solution, an emulsifiable concentrate, a wettable powder, a dust or granules.

Further, if desired, other herbicides, insecticides, bacteriocide, plant regulating agents or synergism agents may be combined at the time of the preparation of the formulations or at the time of application of the herbicides.

As other herbicides to be combined with the herbicide of the present invention, there may be mentioned, for instance, 3-(4-methylphenetyloxyphenyl)-1-methyl-1-methoxyurea and the compound disclosed in Farm Chemicals Handbook, 67 Eddition (1981).

Examples of formulations of the herbicides containing the compounds of the present invention as an active ingredient, will be given. In the following formulation examples, "parts" means "parts by weight".

EXAMPLES

Formulation Example 1

| Wettable powder | |
|---|---|
| Compound No. 1 of the present invention | 50 parts |
| Zeeklite A (trade name for a kaolin-type clay powder, manufactured by Zeaklite Industries, Co., Ltd.) | 46 parts |
| Sorpol 5039 (trade name for a nonionic cation surfactant, manufactured by Toho Chemical Co., Ltd.) | 2 parts |
| Carplex (trade name for a coagulation-preventing agent composed of a mixture of a surfactant with white carbon, manufactured by Shionogi Pharmaceutical Co., Ltd.) | 2 parts |

The above ingredients are homogeneously pulverized and mixed to form a wettable powder.

Formulation Example 2

| Emulsifiable concentrate | |
|---|---|
| Compound No. 2 of the present invention | 20 parts |
| Xylene | 75 parts |
| Sorpol 2680 (trade name for a mixture of a nonionic surfactant and a cationic surfactant) | 5 parts |

The above ingredients are homogeneousely mixed to obtain an emulsifiable concentrate.

The process for producing the compounds of the present invention will be described in detail with reference to the Examples.

EXAMPLE 1

2-[1-(3-difluoromethoxyphenyl)ethylsulfonyl]pyridine-N-oxide

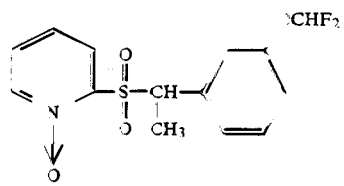

(Compound No. 2 of the present invention)

1.95 g of 2-(3-difluoromethoxybenzylsulfonyl)pyridine-N-oxide was portion-wise added under cooling with ice to 50 ml of a dimethylformamide solution containing 280 mg of 55% sodium hydride. Upon completion of the generation of hydrogen gas, 930 mg of methyl iodide was added to the dark red solution and the mixture was left at room temperature for 20 minutes. Thereafter, a saturated ammonium chloride aqueous solution was gradually added under cooling with ice to complete the reaction.

Then, the reaction mixture was extracted with 200 ml of benzene, washed with water, dried and then concentrated under reduced pressure to obtain light yellow crystals. This crude product was purified by column chromatography to obtain 1.4 g of the desired Compound No. 2 of the present invention. The final product was white crystals having a melting point of from 135° to 137° C.

EXAMPLE 2

2-[1-(2-difluoromethoxy-5-chlorophenyl)ethylsulfonyl]pyridine-N-oxide

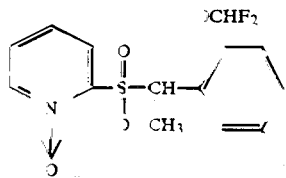

(Compound No. 15 of the present invention)

In the same manner as in Example 1, 8.86 g of 2-(2-difluoromethoxy-5-chlorobenzylsulfonyl)pyridine-N-oxide, 1.11 g of 55% sodium hydride and 3.60 g of methyl iodide were mixed with 150 ml of dimethylformamide and the mixture was reacted followed by the same after-treatment as in Example 1, whereby 7.00 g of Compound No. 15 of the present invention was obtained. The product was white crystals having a melting point of from 145°-147° C.

EXAMPLE 3

2-[1-(2-(2,2,2-trifluoroethoxy)-5-chlorophenyl)ethylsulfonyl]pyridine-N-oxide

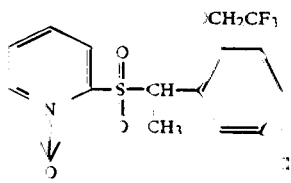

-continued
(Compound No. 27 of the present invention)

In the same manner as Example 1, 2.00 g of 2-[2-(2,2,2-trifluoroethoxy)-5-chlorobenzylsulfonyl]pyridine-N-oxide, 230 mg of 55% sodium hydride and 740 mg of methyl iodide were mixed with 50 ml of dimethylformamide and the mixture was reacted, followed by the same after-treatment as in Example 1, whereby 1.43 g of Compound No. 27 of the present invention was obtained. The product was white crystals having a melting point of from 119° to 121° C.

EXAMPLE 4

4-methyl-2-[1-(2-difluoromethoxy-5-chlorophenyl)ethylsulfonyl)]pyridine-N-oxide

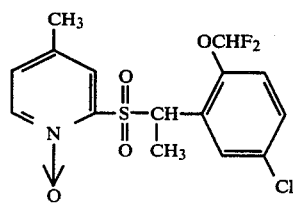

(Compound No. 52 of the present invention)

In the same manner as in Example 1, 800 g of Compound No. 52 of the present invention was obtained from 1.20 g of 4-methyl-2-(2-difluoromethoxy-5-chlorobenzylsulfonyl)pyridine-N-oxide, 140 mg of 55% sodium hydride and 460 mg of methyl iodide. The product was white crystals having a melting point of from 206°–208° C.

EXAMPLE 5

4-methyl-2-[1-(2-(2,2,2-trifluoroethoxy)-5-chlorophenyl)ethylsulfonyl)]pyridine-N-oxide

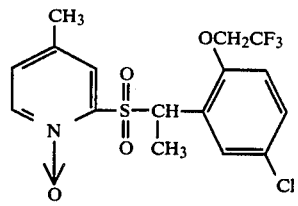

(Compound No. 59 of the present invention)

(1) In the same manner as in Example 1, 1.90 g of Compound No. 59 of the present invention was obtained from 2.30 g of 4-methyl-2-[2-(2,2,2-trifluoroethoxy)-5-chlorobenzyl]pyridine-N-oxide, 280 mg of 55% sodium hydride and 0.92 g of methyl iodide. The product was white crystals having a melting point of from 163° to 165° C.

(2) 7.82 g of 1-[2-(2,2,2-trifluoroethoxy)-5-chlorophenyl]ethylbromide, 3.50 g of 2-mercapto-4-methyl-pyridine-N-oxide and 1.87 g of 85% KOH were dissolved in 100 ml of methanol and the solution was heated under reflux for 30 minutes. The reaction mixture thereby obtained was subjected to a usual after-treatment, whereby 8.90 g of oily substance of 4-methyl-[1-(2-(2,2,2-trifluoroethoxy)-5-chlorophenyl)ethylthio]pyridine-N-oxide was obtained. The yield was 91%. Then, 8.90 g of the above oily substance and 14.40 g of m-chloroperbenzoic acid was dissolved under cooling in 200 ml of chloroform and then left at room temperature for one day and night. After the completion of the reaction, the chloroform solution was washed with a sodium hydrogen carbonate aqueous solution and then with water and dried and then the chloroform solution was concentrated under reduced pressure to obtain 8.70 g of crude crystals of Compound No. 59 of the present invention. These crude crystals were purified by column chromatography, whereby 7.60 g of Compound No. 59 of the present invention was obtained. The product was white crystals having a melting point of from 163° to 165° C.

The compounds prepared in a manner similar to Examples 1 to 5 are shown in Table 2.

TABLE 2

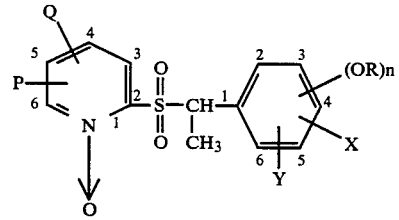

| Comp. No. | RO | n | X | Y | P | Q | Characteristics | Melting point (°C.) |
|---|---|---|---|---|---|---|---|---|
| 1 | 2-CHF$_2$O | 1 | H | H | H | H | Viscous oily substance | |
| 2 | 3-CHF$_2$O | 1 | H | H | H | H | White crystal | 135–137 |
| 3 | 4-CHF$_2$O | 1 | H | H | H | H | " | 152–154 |
| 4 | 2-CF$_3$CH$_2$O | 1 | H | H | H | H | " | 136–138 |
| 13 | 2-CHF$_2$O | 1 | 3-Cl | H | H | H | " | 140–143 |
| 15 | 2-CHF$_2$O | 1 | 5-Cl | H | H | H | " | 145–147 |
| 16 | 2-CHF$_2$O 6-CHF$_2$O | 2 | H | H | H | H | " | 121–123 |
| 17 | 2-CHF$_2$O | 1 | 5-F | H | H | H | " | 152–154 |

TABLE 2-continued

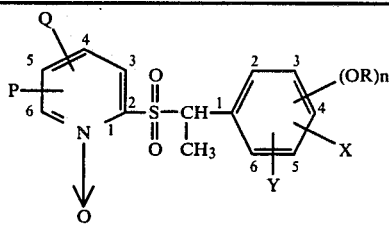

| Comp. No. | RO | n | X | Y | P | Q | Characteristics | Melting point (°C.) |
|---|---|---|---|---|---|---|---|---|
| 18 | 2-CHF$_2$O | 1 | 5-Br | H | H | H | " | 165–167 |
| 19 | 2-CHF$_2$O | 1 | 5-CH$_3$ | H | H | H | " | 126–128 |
| 23 | 3-CHF$_2$O | 1 | 6-Cl | H | H | H | " | 147–149 |
| 24 | 3-CHF$_2$O 4-CHF$_2$O | 2 | H | H | H | H | " | 115–118 |
| 27 | 2-CF$_3$CH$_2$O | 1 | 5-Cl | H | H | H | " | 119–121 |
| 29 | 2-CF$_3$CH$_2$O 6-CF$_3$CH$_2$O | 2 | H | H | H | H | " | 137–140 |
| 30 | 3-CF$_3$CH$_2$O | 1 | 6-Cl | H | H | H | " | 155–158 |
| 31 | 2-CF$_3$CH$_2$O | 1 | 5-F | H | H | H | " | 110–113 |
| 32 | 2-CF$_3$CH$_2$O | 1 | 5-Br | H | H | H | " | 132–134 |
| 33 | 2-CF$_3$CH$_2$O | 1 | 5-CH$_3$ | H | H | H | Viscous oily substance | |
| 34 | 2-CF$_3$CH$_2$O | 1 | 5-C$_2$H$_5$ | H | H | H | Viscous oily substance | |
| 38 | 2-ClCH$_2$CH$_2$O | 1 | 5-Cl | H | H | H | Viscous oily substance | |
| 39 | 2-ClCH$_2$CH$_2$O | 1 | 6-Cl | H | H | H | Viscous oily substance | |
| 40 | 2-Cl(CH$_2$)$_3$O | 1 | 5-Cl | H | H | H | White crystal | 94–98 |
| 44 | 2-CHF$_2$O | 1 | 3-Cl | 5-Cl | H | H | " | 168–170 |
| 45 | 2-CHF$_2$O | 1 | 3-Cl | 5-Br | H | H | " | 153–155 |
| 47 | 2-CHF$_2$O | 1 | 5-Cl | H | 3-CH$_3$ | H | " | 134–136 |
| 52 | 2-CHF$_2$O | 1 | 5-Cl | H | 4-CH$_3$ | H | " | 206–208 |
| 55 | 2-CHF$_2$O | 1 | 5-F | H | 4-CH$_3$ | H | " | 202–204 |
| 56 | 2-CHF$_2$O | 1 | 5-Br | H | 4-CH$_3$ | H | " | 208–210 |
| 57 | 2-CHF$_2$O | 1 | 5-CH$_3$ | H | 4-CH$_3$ | H | " | 185–188 |
| 59 | 2-CF$_3$CH$_2$O | 1 | 5-Cl | H | 4-CH$_3$ | H | " | 163–165 |
| 61 | 2-CF$_3$CH$_2$O | 1 | 5-F | H | 4-CH$_3$ | H | " | 175–178 |
| 62 | 2-CF$_3$CH$_2$O | 1 | 5-Br | H | 4-CH$_3$ | H | " | 144–147 |
| 63 | 2-CF$_3$CH$_2$O | 1 | 5-CH$_3$ | H | 4-CH$_3$ | H | " | 125–129 |
| 82 | 2-CHF$_2$O | 1 | 5-Cl | H | 5-CH$_3$ | H | Viscous oily substance | |
| 84 | 3-CHF$_2$O | 1 | 6-Cl | H | 5-CH$_3$ | H | White crystal | 180–181 |
| 88 | 2-CF$_3$CH$_2$O | 1 | 5-C$_2$H$_5$ | H | 4-CH$_3$ | H | " | 99–101 |

Now, the effectiveness of the herbicidal compounds of the present invention as compared with compounds of the prior art represented by Comparative Compounds A, B and C will be described in detail with reference to Test Examples.

Comparative Compound A

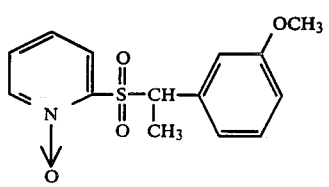

(White crystals having a melting point of from 102 to 105° C.)

Comparative Compound B

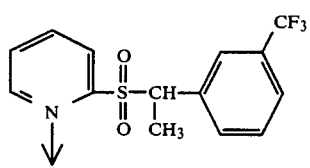

(White crystals having a melting point of from 97 to 99° C.)

Comparative Compound C

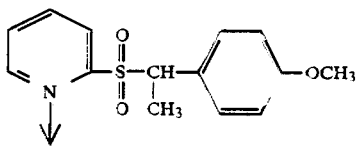

(White crystals having a melting point of from 136 to 138° C.)

TEST EXAMPLE 1

Test on the herbicidal effects in soil treatment

A plastic box having a length of 15 cm, a width of 22 cm, and a depth of 6 cm was filled with a sterilized diluvium soil, and seeds of barnyardgrass, large crabgrass, green foxtail and cyperus microiria were sown. Further, purpole nutsedge tubers were further planted. The soil was covered thereon in the thickness of about 1.5 cm and then a solution was applied on to the surface of the soil to distribute the active ingredient uniformly at a predetermined concentration.

Each solution was prepared by diluting the wettable powder or emulsifiable concentrate described in the above Formulation Examples with water and sprayed onto the entire soil surface by means of a small spray. Three weeks after the application of the solution, the herbicidal effects against each weed were determined on the basis of following standard rating. The results thereby obtained are shown in Table 3.

Standard rating

5 ... Growth control rate of more than 90% (almost completely withered)
4 ... Growth control rate of from 70 to 90%
3 ... Growth control rate of from 40 to 70%
2 ... Growth control rate of from 20 to 40%
1 ... Growth control rate of from 5 to 20%
0 ... Growth control rate of less than 5% (almost non-effective)

The above growth control rates were calculated by the following equation:

$$\text{Growth control (\%)} = \left(1 - \frac{\text{Weight of the weed grown above the soil surface of the treated area}}{\text{Weight of the weed grown above the soil surface of the non-treated area}}\right) \times 100$$

TABLE 3

| Comp. No. | Dose (kg/ha) | Ba. | L.C. | G.F. | C.M. | P.N. |
|---|---|---|---|---|---|---|
| 1 | 0.5 | 5 | 5 | 5 | 5 | 5 |
|  | 0.25 | 5 | 5 | 5 | 5 | 4 |
|  | 0.125 | 5 | 5 | 5 | 5 | — |
| 2 | 0.5 | 5 | 5 | 5 | 5 | 5 |
|  | 0.25 | 5 | 5 | 5 | 5 | 4 |
|  | 0.125 | 5 | 5 | 5 | 5 | — |
| 3 | 0.5 | 5 | 5 | 5 | 5 | 5 |
|  | 0.25 | 5 | 5 | 5 | 5 | 4 |
|  | 0.125 | 5 | 5 | 4 | 5 | — |
| 4 | 0.5 | 5 | 5 | 5 | 5 | 5 |
|  | 0.25 | 5 | 5 | 5 | 5 | 4 |
|  | 0.125 | 5 | 5 | 5 | 5 | — |
| 13 | 0.5 | 5 | 5 | 5 | 5 | 4 |
|  | 0.25 | 5 | 5 | 5 | 5 | 4 |
|  | 0.125 | 4 | 5 | 4 | 5 | — |
| 15 | 0.5 | 5 | 5 | 5 | 5 | 5 |
|  | 0.25 | 5 | 5 | 5 | 5 | 5 |
|  | 0.125 | 5 | 5 | 5 | 5 | — |
| 16 | 0.5 | 5 | 5 | 5 | 5 | 5 |
|  | 0.25 | 5 | 5 | 5 | 5 | 4 |
|  | 0.125 | 5 | 5 | 5 | 4 | — |
| 17 | 0.5 | 5 | 5 | 5 | 5 | 5 |
|  | 0.25 | 5 | 5 | 5 | 5 | 5 |
|  | 0.125 | 5 | 5 | 5 | 5 | — |
| 18 | 0.5 | 5 | 5 | 5 | 5 | 5 |
|  | 0.25 | 5 | 5 | 5 | 5 | 4 |
|  | 0.125 | 5 | 5 | 5 | 5 | — |
| 19 | 0.5 | 5 | 5 | 5 | 5 | 5 |
|  | 0.25 | 5 | 5 | 5 | 5 | 5 |
|  | 0.125 | 5 | 5 | 5 | 5 | — |
| 23 | 0.5 | 5 | 5 | 5 | 5 | 5 |
|  | 0.25 | 5 | 5 | 5 | 5 | 4 |
|  | 0.125 | 5 | 5 | 5 | 5 | — |
| 24 | 0.5 | 5 | 5 | 5 | 5 | 4 |
|  | 0.25 | 5 | 5 | 5 | 5 | 4 |
|  | 0.125 | 5 | 5 | 5 | 4 | — |
| 27 | 0.5 | 5 | 5 | 5 | 5 | 5 |
|  | 0.25 | 5 | 5 | 5 | 5 | 5 |
|  | 0.125 | 5 | 5 | 5 | 5 | — |
| 29 | 0.5 | 5 | 5 | 5 | 5 | 5 |
|  | 0.25 | 5 | 5 | 5 | 5 | 4 |
|  | 0.125 | 5 | 5 | 5 | 5 | — |
| 30 | 0.5 | 5 | 5 | 5 | 5 | 4 |
|  | 0.25 | 4 | 5 | 4 | 5 | 4 |
|  | 0.125 | 4 | 4 | 4 | 5 | — |
| 31 | 0.5 | 5 | 5 | 5 | 5 | 5 |
|  | 0.25 | 5 | 5 | 5 | 5 | 5 |
|  | 0.125 | 5 | 5 | 5 | 5 | — |
| 32 | 0.5 | 5 | 5 | 5 | 5 | 5 |
|  | 0.25 | 5 | 5 | 5 | 5 | 5 |
|  | 0.125 | 5 | 5 | 5 | 5 | — |
| 33 | 0.5 | 5 | 5 | 5 | 5 | 5 |
|  | 0.25 | 5 | 5 | 5 | 5 | 5 |
|  | 0.125 | 5 | 5 | 5 | 5 | — |
| 34 | 0.5 | 5 | 5 | 5 | 5 | 5 |
|  | 0.25 | 5 | 5 | 5 | 5 | 5 |
|  | 0.125 | 5 | 5 | 5 | 5 | — |
| 44 | 0.5 | 5 | 5 | 5 | 5 | 5 |
|  | 0.25 | 5 | 5 | 5 | 5 | 4 |
|  | 0.125 | 5 | 5 | 5 | 5 | — |
| 45 | 0.5 | 5 | 5 | 5 | 5 | 5 |
|  | 0.25 | 5 | 5 | 5 | 5 | 4 |
|  | 0.125 | 5 | 5 | 5 | 5 | — |
| 47 | 0.5 | 5 | 5 | 5 | 5 | 5 |
|  | 0.25 | 5 | 5 | 5 | 5 | 4 |
|  | 0.125 | 5 | 5 | 4 | 5 | — |
| 52 | 0.5 | 5 | 5 | 5 | 5 | 5 |
|  | 0.25 | 5 | 5 | 5 | 5 | 5 |
|  | 0.125 | 5 | 5 | 5 | 5 | — |
| 55 | 0.5 | 5 | 5 | 5 | 5 | 5 |
|  | 0.25 | 5 | 5 | 5 | 5 | 5 |
|  | 0.125 | 5 | 5 | 5 | 5 | — |
| 56 | 0.5 | 5 | 5 | 5 | 5 | 5 |
|  | 0.25 | 5 | 5 | 5 | 5 | 5 |
|  | 0.125 | 5 | 5 | 5 | 5 | — |
| 57 | 0.5 | 5 | 5 | 5 | 5 | 5 |
|  | 0.25 | 5 | 5 | 5 | 5 | 5 |
|  | 0.125 | 5 | 5 | 5 | 5 | — |
| 59 | 0.5 | 5 | 5 | 5 | 5 | 5 |
|  | 0.25 | 5 | 5 | 5 | 5 | 5 |
|  | 0.125 | 5 | 5 | 5 | 5 | — |
| 61 | 0.5 | 5 | 5 | 5 | 5 | 5 |
|  | 0.25 | 5 | 5 | 5 | 5 | 5 |
|  | 0.125 | 5 | 5 | 5 | 5 | — |
| 62 | 0.5 | 5 | 5 | 5 | 5 | 5 |
|  | 0.25 | 5 | 5 | 5 | 5 | 5 |
|  | 0.125 | 5 | 5 | 5 | 5 | — |
| 63 | 0.5 | 5 | 5 | 5 | 5 | 5 |
|  | 0.25 | 5 | 5 | 5 | 5 | 5 |
|  | 0.125 | 5 | 5 | 5 | 5 | — |
| 82 | 0.5 | 5 | 5 | 5 | 5 | 4 |
|  | 0.25 | 5 | 5 | 5 | 5 | 4 |
|  | 0.125 | 4 | 4 | 4 | 4 | — |
| 84 | 0.5 | 5 | 5 | 4 | 3 | 3 |
|  | 0.25 | 5 | 5 | 3 | 3 | 2 |
|  | 0.125 | 4 | 4 | 2 | 1 | — |
| 88 | 0.5 | 5 | 5 | 5 | 5 | 5 |
|  | 0.25 | 5 | 5 | 5 | 5 | 5 |
|  | 0.125 | 5 | 5 | 5 | 5 | — |
| A* | 0.5 | 2 | 2 | 1 | 3 | 0 |
|  | 0.25 | 1 | 1 | 0 | 2 | 0 |
|  | 0.125 | 0 | 0 | 0 | 0 | — |
| B* | 0.5 | 3 | 3 | 3 | 3 | 1 |
|  | 0.25 | 1 | 1 | 2 | 2 | 0 |
|  | 0.125 | 0 | 0 | 0 | 0 | 0 |
| C* | 0.5 | 1 | 1 | 0 | 2 | 0 |
|  | 0.25 | 0 | 0 | 0 | 1 | 0 |
|  | 0.125 | 0 | 0 | 0 | 0 | — |

Note:
Ba.: Barnyardgrass
L.C.: Large crab grass
G.F.: Green foxtail
C.M.: Cyperus microiria
P.N.: Purple nutsedge
*Compounds disclosed in U.S. Pat. No. 4019893.

TEST EXAMPLE 2

Test on phytotoxicity against crop plants in soil treatment

A plastic box having a length of 15 cm, a width of 22 cm and a depth of 6 cm was filled with a sterilized diluvium soil, and seeds of sugar beet, rape, soybean and cotton were sown and covered by the soil of a thickness of about 1.5 cm. Then a solution was uniformly applied to the soil surface to distribute the active ingredient in a predetermined dose. Each solution was prepared by diluting the wettable powder or emulsifiable concentrate described in the above Fomulation Examples with water and sprayed to the entire surface by a small spray. Three weeks after the application of the solution, the phytotoxicity against the above crop plants were determined on the basis of the following standard rating. The results thereby obtained are shown in Table 4.

Standard rating

5 ... Complete death of plant
4 ... Serious phytotoxicity to the plant
3 ... Fair phytotoxicity to the plant
2 ... Slight phytotoxicity to the plant
1 ... Extremely slight phytotoxicity to the plant
0 ... No phytotoxicity to the plant

TABLE 4

| Comp. No. | Dose (kg/ha) | Phytotoxicity |||| 
|---|---|---|---|---|---|
| | | Cotton | Soybean | Sugar beet | Rape |
| 1 | 2.0 | 0 | 0 | 0 | 0 |
| | 1.0 | 0 | 0 | 0 | 0 |
| 2 | 2.0 | 0 | 0 | 0 | 0 |
| | 1.0 | 0 | 0 | 0 | 0 |
| 3 | 2.0 | 0 | 0 | 0 | 0 |
| | 1.0 | 0 | 0 | 0 | 0 |
| 4 | 2.0 | 0 | 0 | 0 | 0 |
| | 1.0 | 0 | 0 | 0 | 0 |
| 13 | 2.0 | 0 | 0 | 0 | 0 |
| | 1.0 | 0 | 0 | 0 | 0 |
| 15 | 2.0 | 0 | 0 | 0 | 0 |
| | 1.0 | 0 | 0 | 0 | 0 |
| 16 | 2.0 | 0 | 0 | 0 | 0 |
| | 1.0 | 0 | 0 | 0 | 0 |
| 17 | 2.0 | 0 | 0 | 0 | 0 |
| | 1.0 | 0 | 0 | 0 | 0 |
| 18 | 2.0 | 0 | 0 | 0 | 0 |
| | 1.0 | 0 | 0 | 0 | 0 |
| 19 | 2.0 | 0 | 0 | 0 | 0 |
| | 1.0 | 0 | 0 | 0 | 0 |
| 23 | 2.0 | 0 | 0 | 0 | 0 |
| | 1.0 | 0 | 0 | 0 | 0 |
| 24 | 2.0 | 0 | 0 | 0 | 0 |
| | 1.0 | 0 | 0 | 0 | 0 |
| 27 | 2.0 | 0 | 0 | 0 | 0 |
| | 1.0 | 0 | 0 | 0 | 0 |
| 29 | 2.0 | 0 | 0 | 0 | 0 |
| | 1.0 | 0 | 0 | 0 | 0 |
| 30 | 2.0 | 0 | 0 | 0 | 0 |
| | 1.0 | 0 | 0 | 0 | 0 |
| 31 | 2.0 | 0 | 0 | 0 | 0 |
| | 1.0 | 0 | 0 | 0 | 0 |
| 32 | 2.0 | 0 | 0 | 0 | 0 |
| | 1.0 | 0 | 0 | 0 | 0 |
| 33 | 2.0 | 0 | 0 | 0 | 0 |
| | 1.0 | 0 | 0 | 0 | 0 |
| 34 | 2.0 | 0 | 0 | 0 | 0 |
| | 1.0 | 0 | 0 | 0 | 0 |
| 44 | 2.0 | 0 | 0 | 0 | 0 |
| | 1.0 | 0 | 0 | 0 | 0 |
| 45 | 2.0 | 0 | 0 | 0 | 0 |
| | 1.0 | 0 | 0 | 0 | 0 |
| 47 | 2.0 | 0 | 0 | 0 | 0 |
| | 1.0 | 0 | 0 | 0 | 0 |
| 52 | 2.0 | 0 | 0 | 0 | 0 |
| | 1.0 | 0 | 0 | 0 | 0 |
| 55 | 2.0 | 0 | 0 | 0 | 0 |
| | 1.0 | 0 | 0 | 0 | 0 |
| 56 | 2.0 | 0 | 0 | 0 | 0 |
| | 1.0 | 0 | 0 | 0 | 0 |
| 57 | 2.0 | 0 | 0 | 0 | 0 |
| | 1.0 | 0 | 0 | 0 | 0 |
| 59 | 2.0 | 0 | 0 | 0 | 0 |

TABLE 4-continued

| Comp. No. | Dose (kg/ha) | Phytotoxicity |||| 
|---|---|---|---|---|---|
| | | Cotton | Soybean | Sugar beet | Rape |
| | 1.0 | 0 | 0 | 0 | 0 |
| 61 | 2.0 | 0 | 0 | 0 | 0 |
| | 1.0 | 0 | 0 | 0 | 0 |
| 62 | 2.0 | 0 | 0 | 0 | 0 |
| | 1.0 | 0 | 0 | 0 | 0 |
| 63 | 2.0 | 0 | 0 | 0 | 0 |
| | 1.0 | 0 | 0 | 0 | 0 |
| 82 | 2.0 | 0 | 0 | 0 | 0 |
| | 1.0 | 0 | 0 | 0 | 0 |
| 84 | 2.0 | 0 | 0 | 0 | 0 |
| | 1.0 | 0 | 0 | 0 | 0 |
| 88 | 2.0 | 0 | 0 | 0 | 0 |
| | 1.0 | 0 | 0 | 0 | 0 |

TEST EXAMPLE 3

Test on herbicidal effects and phytotoxicity in foliage treatment

A plastic box having a length of 30 cm, a width of 22 cm and a depth of 6 cm was filled with a sterilized diluvium soil, and weed seeds of barnyardgrass, large crab grass, green foxtail as well as crop plant seeds of cotton, soybean and sugar beet were spot-wisely sown. Further, purple nutsedge tubers are planted and then the soil was covered thereon in a thickness of about 1.5 cm. When the various weeds and crop plant grew to the 2–3 leaf stage, a solution was uniformly sprayed on the foliages to distribute the active ingredient in a predetermined dose. Each solution was prepared by diluting the wettable powder or emulsifiable concentrate described in above Formulation Examples with water and sprayed to the entire surface of the foliages of the weeds and the crop plants by a small spray. Four weeks after the application of the solution, the herbicidal effects against each weeds were determined on the basis of the standard rating described in Test Example 1 and the phytotoxicity against each crop plant was determined on the basis of the standard rating described in Test Example 2. The results thereby obtained are shown in Table 5.

TABLE 5

| Comp. No. | Dose (kg/ha) | Herbicidal effects ||||| Phytotoxicity |||
|---|---|---|---|---|---|---|---|---|---|
| | | Ba. | L.C. | G.F. | B.G. | P.N. | Soy-bean | Cot-ton | Sugar beet |
| 4 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 15 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 16 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 17 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 18 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 19 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 23 | 1.0 | 5 | 5 | 5 | — | 5 | 0 | 0 | 0 |
| | 0.5 | 5 | 5 | 5 | — | 5 | 0 | 0 | 0 |
| | 0.25 | 4 | 5 | 5 | — | 5 | 0 | 0 | 0 |
| 27 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | — | 5 | 0 | 0 | 0 |

TABLE 5-continued

| Comp. No. | Dose (kg/ha) | Herbicidal effects | | | | | Phytotoxicity | | |
|---|---|---|---|---|---|---|---|---|---|
| | | Ba. | L.C. | G.F. | B.G. | P.N. | Soybean | Cotton | Sugar beet |
| 29 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 31 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 32 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 33 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 34 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 55 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 56 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 57 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 61 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 62 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 63 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 88 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 1 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 2 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 3 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 13 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 24 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 30 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 44 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 45 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 47 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 52 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 59 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 82 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| 84 | 1.0 | 5 | 5 | 5 | 5 | 5 | 0 | 0 | 0 |
| | 0.5 | 5 | 5 | 5 | 5 | 5 | 0 | 0 | 0 |
| | 0.25 | 5 | 5 | 5 | 5 | 5 | 0 | 0 | 0 |
| A* | 1.0 | 1 | 0 | 0 | 0 | 0 | 0 | 0 | 0 |
| | 0.5 | 0 | 0 | 0 | 0 | 0 | 0 | 0 | 0 |
| | 0.25 | 0 | 0 | 0 | 0 | 0 | 0 | 0 | 0 |
| C* | 1.0 | 0 | 0 | 0 | 0 | 0 | 0 | 0 | 0 |
| | 0.5 | 0 | 0 | 0 | 0 | 0 | 0 | 0 | 0 |
| | 0.25 | 0 | 0 | 0 | 0 | 0 | 0 | 0 | 0 |

Note:
Ba. Barnyardgrass
L.C. Large crabgrass
G.F. Green foxtail
B.G. Black grass
P.N. Purple nutsedge

*Compounds disclosed in U.S. Pat. No. 4,019,893.

We claim:

1. A 1-Phenylethyl sulfone substituted by a halogenated alkyloxy group, represented by the formula

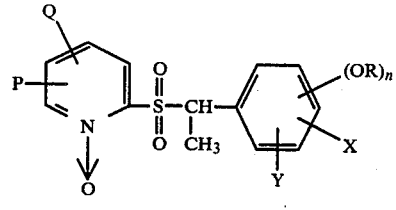

wherein
R is lower alkyl substituted by halogen,
n is 1 or 2,
each of P and Q is a hydrogen atom or lower alkyl and
each of X and Y is hydrogen, lower alkyl or halogen.

2. A herbicidal composition comprising:
(a) an herbicidally effective amount of a 1-phenylethyl sulfone substituted by a halogenated alkyloxyl group, of the formula

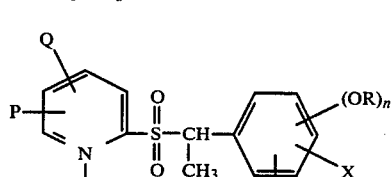

wherein
R is lower alkyl susbstituted by halogen,
n is 1 or 2,
each of P and Q is hydrogen or lower alkyl, and
each of X and Y is hydrogen, lower alkyl or halogen; and
(b) a herbicidally acceptable carrier.

3. The herbicidal composition of claim 2, wherein the carrier is selected from the group consisting of clay, talc, bentonite, diatomaceous earth, water, an alcohol, an aromatic hydrocarbon, a chlorinated hydrocarbon, an ether, a ketone, an ester, and an acid amide.

4. The herbicidal composition of claim 3 wherein:
the alcohol is methanol or ethanol;
the aromatic hydrocarbon is benzene, toluene or xylene;
the ester is ethyl acetate; and
the acid amide is dimethyl formamide.

5. The herbicidal composition of claim 2 further comprising:
an emulsifier;
a dispersing agent;
a suspending agent;
a penetrating agent;
a spreader; or
a stabilizer.

6. The herbicidal composition of claim 5 in the form of:
a solution;
an emulsifiable concentrate;
a wettable powder; a dust; or
granules.

* * * * *